(12) United States Patent
Cowan et al.

(10) Patent No.: US 7,894,904 B2
(45) Date of Patent: *Feb. 22, 2011

(54) SYSTEMS AND METHODS FOR IMPLANTABLE LEADLESS BRAIN STIMULATION

(75) Inventors: Mark W. Cowan, Fremont, CA (US); Richard E. Riley, Palo Alto, CA (US); Axel F. Brisken, Fremont, CA (US); Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/764,602

(22) Filed: Jun. 18, 2007

(65) Prior Publication Data

US 2007/0293908 A1    Dec. 20, 2007

Related U.S. Application Data

(60) Provisional application No. 60/805,320, filed on Jun. 20, 2006.

(51) Int. Cl.
*A61N 1/08* (2006.01)
(52) U.S. Cl. .......... 607/45
(58) Field of Classification Search .......... 607/45, 607/60, 61
See application file for complete search history.

(56) References Cited

U.S. PATENT DOCUMENTS

| 5,405,367 | A | 4/1995 | Schulman et al. |
|---|---|---|---|
| 5,716,377 | A | 2/1998 | Rise et al. |
| 5,782,798 | A | 7/1998 | Rise |
| 6,016,449 | A | 1/2000 | Fischell et al. |
| 6,037,704 | A | 3/2000 | Welle |
| 6,366,816 | B1 | 4/2002 | Marchesi |
| 6,427,086 | B1 | 7/2002 | Fischell et al. |
| 7,010,351 | B2 | 3/2006 | Firlik et al. |
| 7,013,177 | B1 | 3/2006 | Whitehurst et al. |
| 2004/0172083 | A1* | 9/2004 | Penner .......... 607/35 |
| 2004/0204744 | A1* | 10/2004 | Penner et al. .......... 607/23 |
| 2006/0136004 | A1* | 6/2006 | Cowan et al. .......... 607/33 |

FOREIGN PATENT DOCUMENTS

DE    4330680    3/1995

* cited by examiner

*Primary Examiner*—Eric D. Bertram
(74) *Attorney, Agent, or Firm*—Kilpatrick Townsend & Stockton LLP

(57) ABSTRACT

Systems and methods are disclosed to stimulate brain tissue to treat medical conditions such as movement disorders, pain and epilepsy. The disclosed invention uses electrical stimulation of the brain tissue, where vibrational energy from a source is received by an implanted device and converted to electrical energy and the converted electrical energy is used by implanted electrodes to stimulate the pre-determined brain site. The vibrational energy is generated by a controller-transmitter, which could be either implanted or located externally. The vibrational energy is received by a receiver-stimulator, which could be located under the skull, within the brain, on the dura, or in the cranial space close to the brain. As a therapeutic treatment, the implantable receiver-stimulator stimulates the brain sites that are effective in altering brain activity.

18 Claims, 3 Drawing Sheets

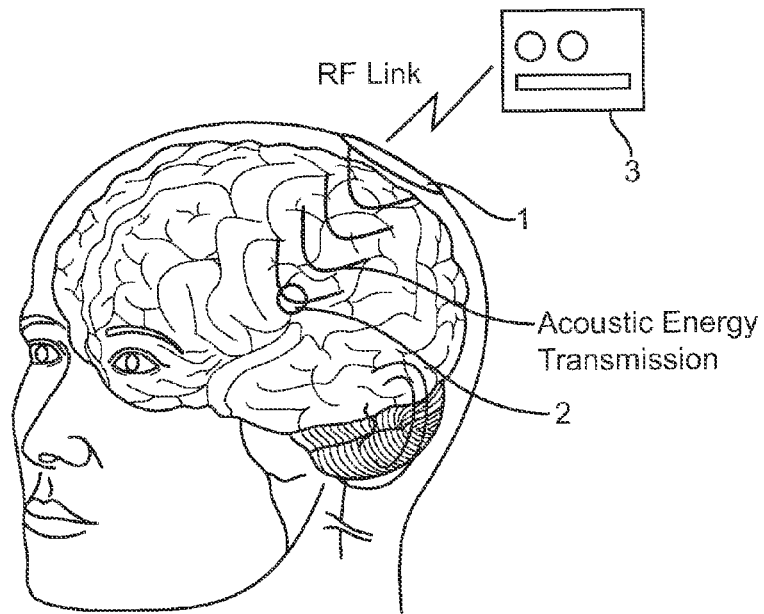
FIG. 1
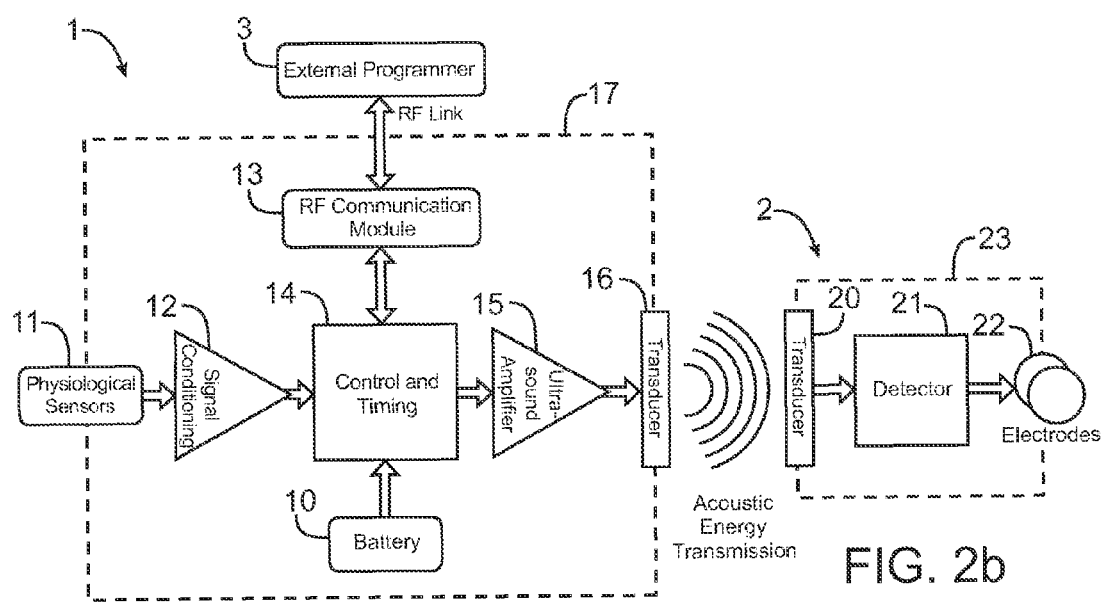
FIG. 2a
FIG. 2b

SYSTEMS AND METHODS FOR IMPLANTABLE LEADLESS BRAIN STIMULATION

CROSS-REFERENCES TO RELATED APPLICATIONS

The present application claims the benefit of provisional U.S. Application No. 60/805,320, filed Jun. 20, 2006, the full disclosure of which is incorporated herein by reference.

BACKGROUND OF THE INVENTION

1. Field of the Invention

The systems and methods of this invention relate to direct electrical stimulation of brain tissue for treatment of a variety medical conditions. Specifically, the present invention relates to methods and apparatus for applying such stimulation without the use of conventional lead/electrode systems.

2. Description of the Background Art

Electrical stimulation of brain tissue is a growing treatment for many neurological disorders, including alleviation of Parkinson's and essential tremor diseases, chronic pain, depression, epileptic seizures, motor dysfunction due to stroke, and other emerging applications such as diabetes, obesity, and urinary control. Treatment regimens and targeted brain tissue locations are becoming known in related art through use of current, common stimulation devices and methods. Commonly implanted devices for direct brain stimulation are made by such companies as Medtronic, Cyberonics, and NeuroPace.

Deep Brain Stimulation (DBS) generally refers to treatments for a variety of medical conditions that apply electrical stimulation directly on brain tissue or in regions of the brain. Currently available stimulators for DBS are battery-powered electronic devices implanted under the skin that are connected via insulated metal lead(s) to electrodes that are inserted into or onto the brain. DBS uses the inserted electrodes to deliver a variety of stimulation modalities. For example, continuous high-frequency electrical stimulation is used in areas of the brain including the thalamus, globus pallidus (GPi), or the subthalamic nucleus (STN), or other parts of the brain to control movement disorders. High frequency stimulation of cells in these areas actually shuts them down, helping to rebalance control messages throughout the movement control centers in the brain.

DBS of the thalamus is primarily used to treat disabling tremor, especially tremor that affects one side of the body substantially more than the other. Studies have shown that DBS may significantly reduce tremor in about two thirds of patients with Parkinson's disease (PD). Tremor may not be eliminated, and may continue to cause some impairment. DBS of the globus pallidus is useful in treatment of dyskinesias as well as tremor, and may improve other symptoms, as well. DBS of the subthalamic nucleus may have an effect on most of the main motor features of PD, including bradykinesia, tremor, and rigidity.

Treatment sites for movement disorders may be identified by probing brain tissue and a site predetermined for treatment is selected. As noted for movement disorders, published regions of the brain include, but are not limited to, the ventral intermediate thalamus, subthalamic nucleus, and internal globus pallidus.

Similarly, DBS has been pursued as a treatment for pain for the past 30 years. Peripheral pain signals are transmitted via the spinothalamic tract of the spinal cord and synapse primarily in the thalamus. Thus, the area where they synapse was seen as a prime target for DBS and was the focus of much of the early research. DBS continues to be pursued as a therapy in chronic pain patients. Today, the pain indications that either exist or seem most promising for potential treatment by deep brain stimulation include: neuropathic pain; Complex Regional Pain Syndrome (CRPS), Type II; steady, burning pain; lancinating, shooting pain; tactile hypersensitivity; or partial or complete sensory loss. The targets for DBS for pain typically include the following sites:

Neuropathic Pain
Medial Lemniscus
Ventrobasal (VB) area of the thalamus, including the ventral posteromedial (VPM) and the ventral posterolateral (VPL) nuclei
Internal Capsule
Motor Cortex
Cingulate gyrus (also known as cingulate cortex)
Posterior complex of the thalamus (PO)
Ventrolateral nucleus of the thalamus (VL)
Nociceptive Pain:
Periventricular grey (PVG) matter and periaqueductal grey (PAG) matter, which are sometimes simply called periventricular grey and periaqueductal grey Similar targets in the brain are emerging for other DBS applications. Published targets for the treatment of depression would include, but are not limited to, one or more of the cerebellar vermis, the anterior cingulate gyrus, the dorsal prefrontal cortex, the dorsal raphe nuclei, the median raphe nuclei, and the locus coeruleus. Published targets for the treatment of epilepsy, obesity, and diabetes would include, but are not limited to, the nucleus of tractus solitarius (NTS), the sub thalamic nucleus, the hippocampus, the medial thalamus and the temporal lobe.

Upper regions of the brain, e.g., the cortex, that have been affected by stroke or injury also benefit from stimulation treatments and have been shown to be effective in rehabilitating motor performance of distal extremities. In this stroke rehabilitation treatment the electrode is placed on the dura, the membrane that covers the brain, and used to deliver stimulation to the cortex.

Currently available DBS devices are battery-powered electronic devices implanted under the skin connected via insulated metal lead(s) to electrodes which are inserted into the brain. The brain electrodes are placed into brain tissue via a small cranial hole and then connected to lead extensions which are subcutaneously tunneled between the skull and skin, down the back of the head, and around the neck to the battery-powered pulse generator (also referred to as a controller) that is implanted in a subcutaneous pocket in the pectoral region of the chest. Even in cases where the pulse generator may be located under, within, or on the skull the electrodes are still in direct connection to the pulse stimulator using a lead. The use of these lead wires is associated with significant problems such as complications due to infection, lead failure, and electrode/lead dislodgement.

There have been reported attempts to deal with the complications and limitations imposed by the use of electrical leads. For example, self-contained implantable microstimulators and remotely powered microstimulators have been described; however, each approach suffers from some significant limitation. A self-contained microstimulator must incorporate a battery or some other power supply; this imposes constraints on size, device lifetime, available stimulation energy, or all three. Often, DBS devices contain rechargeable batteries due to high use or high energy requirements of the therapeutic stimulation. Implantation of the pulse generator into the skull has been proposed, which addresses the difficult procedural task of tunneling leads and avoids cosmetic appearance issues associated with the subcutaneous leads and pulse generators; however, the lead still must be placed into the brain and connected to the pulse generator.

For leadless solutions in other similar stimulation applications, remotely powered devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of power (devices with capacity in excess of 20 Watts have been produced), but again relies on close proximity between transmitting and receiving coils, or the utilization of relatively large devices for deeper (5-8 cm maximum) implantation.

The methods and apparatus of the current invention utilize vibrational energy, particularly at ultrasonic frequencies, to overcome many of the limitations of currently known solutions for DBS, by achieving a brain stimulation capability without the use of leads connected to a stimulation controller/pulse generator.

The following patents, all of which are incorporated in this disclosure in their entirety, describe various aspects of using electrical stimulation for achieving various beneficial effects. U.S. Pat. No. 5,716,377 titled "Method of Treating Movement Disorders by Brain Stimulation" by Rise et al. describes a typical implantable DBS system for treating movement disorders such as Parkinson's. U.S. Pat. No. 7,013,177 titled "Treatment of Pain by Brain Stimulation" by Whitehurst et al. describes an implantable DBS system that uses electrical stimulation in the form of a microstimulator in combination with drug delivery for the treatment of pain. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation. U.S. Pat. No. 7,010,351 titled "Methods and apparatus for effectuating a lasting change in a neural-function of a patient" by Firlik et al. describes a DBS system used to treat or effectuate changes to neural function particularly by stimulation in the region of the cortex. U.S. Pat. No. 6,427,086 titled "Means and method for the intracranial placement of a neurostimulator" by Fischell et al. describes a DBS device implanted in the skull. U.S. Pat. No. 6,016,449 titled "System for treatment of neurological disorders" by Fischell et al. describes the use of a DBS device for the treatment of epilepsy. U.S. Pat. No. 5,782,798 titled "Techniques for treating eating disorders by brain stimulation and drug infusion" by Rise describes a DBS system for treating eating disorders with electrical stimulation in regions of the brain.

BRIEF SUMMARY OF THE INVENTION

This invention relates to methods and devices for using electrical stimulation of brain tissues to treat various neurological disorders, dysfunction, and neural activities and using vibrational energy as a means to transmit energy and signal information from a first device, which is implanted, to a second device containing means to receive such vibrational energy and converting it into electrical energy and then apply that electrical energy to stimulating electrodes. The second device is intended to be either permanently or temporarily implanted with stimulating electrodes in direct contact with the brain tissue or in close proximity to the tissue or brain region to be stimulated.

This application of leadless electrical stimulation relates to deep brain stimulation, where the stimulation acts on the brain to reduce symptoms or effectuate change in the neural response of the brain. The invention is a system comprising a controller-transmitter, an implanted receiver-stimulator, and stimulation electrodes, such that the stimulation electrodes would be in contact with brain tissue, in close proximity to the tissue or brain region to be stimulated to facilitate treatment. Stimulating devices incorporating the concepts presented herein have advantages over currently available devices, particularly by eliminating the requirement for electrical leads, and by providing the capability for simultaneous or sequenced stimulation of multiple sites.

In one embodiment, the controller-transmitter could be implanted. The controller-transmitted could be implanted between the skull and the skin or it could be adapted to be implanted under the skull or yet it could be adapted to be implanted in a section of skull that has been removed. In another embodiment, the controller-transmitter could be applied on the external surface of the head. The transmitted vibrational energy would be directed to the receiver-stimulator to cause electrical stimulation at the electrodes of the receiver-stimulator.

An example of use for an external use of the controller-transmitter is for pain management of chronic recurring but not continuous pain. Miniaturized receiver-stimulator devices are implanted, but the controller-transmitter unit is external to the brain, possibly hand-held or worn attached to a belt or harness. The acoustic energy from the external controller-transmitter is coupled through the skin as well as any underlying tissues, to the implanted device. The external controller-transmitter is under control of the patient. Thus, when the patient begins to feel discomfort, the controller-transmitter unit is applied and/or switched on, and certain characteristics, for example the level of stimulating energy and possibly the frequency or pulse duration of the stimulating waveform, is modified by the user, enabling the user to tailor the stimulation as needed to diminish the pain. Similar utility under patient control would be useful for tremor or seizure and the like.

BRIEF DESCRIPTION OF THE DRAWINGS

FIG. 1 is a schematic showing the leadless stimulation system for deep brain stimulation.

FIGS. 2a and 2b are block diagrams showing the components of the acoustic controller-transmitter and acoustic receiver-stimulators of the present invention.

DETAILED DESCRIPTION OF THE INVENTION

Figure 3:
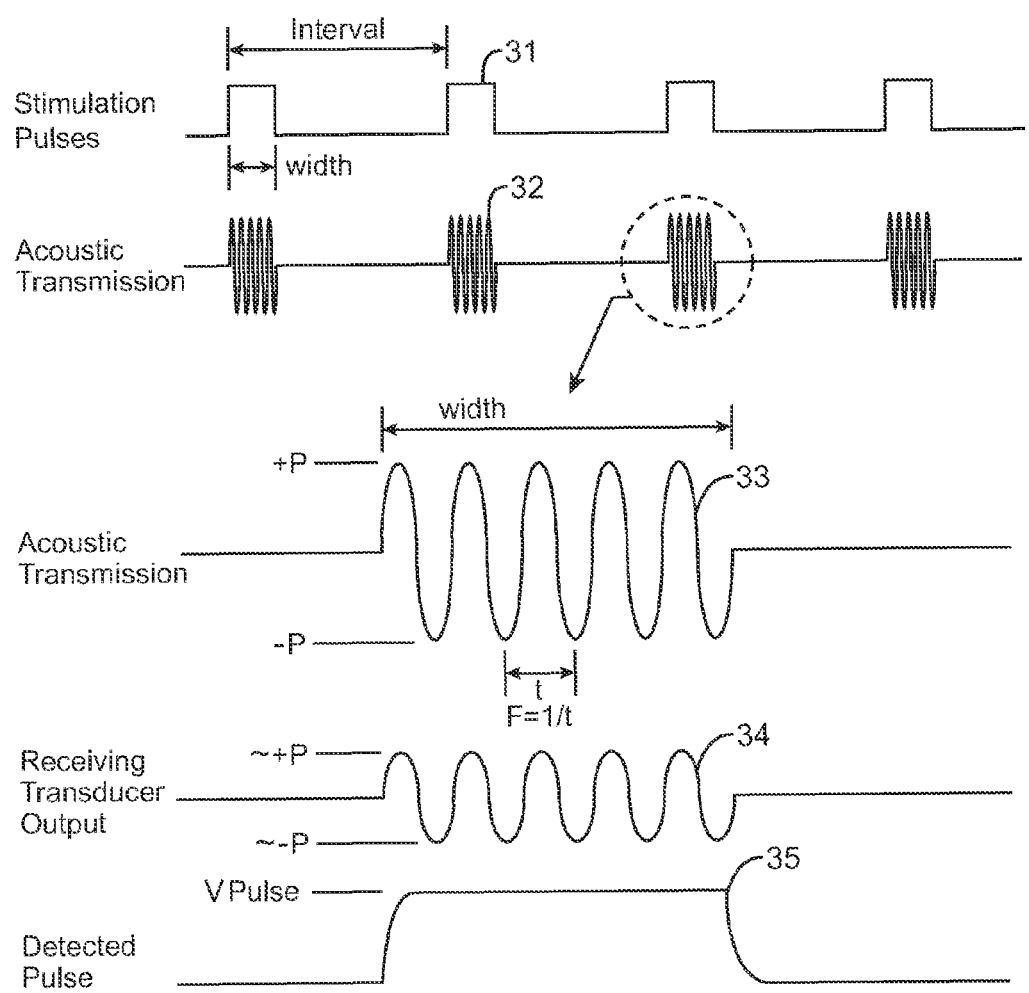
FIG. 3 illustrates representative acoustic and electrical signals useful in the systems and methods of the present invention.

The systems and devices described here comprise a controller-transmitter device that will deliver vibrational energy and information to one or more implanted receiver-stimulator device(s) that will convert the vibrational energy to electrical energy of a form that can be used to electrically stimulate brain tissue. The vibrational energy can be applied with ultrasound as a single burst or as multiple bursts or as a continuous wave with appropriate selection of the following parameters:

| Parameter | Value Range |
| --- | --- |
| Ultrasound frequency | 20 kHz-10 MHz |
| Burst Length (#cycles) | 3-Continuous |
| Stimulation Pulse Duration | 0.1 μsec-Continuous |
| Duty Cycle | 0-100% |
| Mechanical Index | ≦1.9 |

The controller-transmitter device would contain one or more ultrasound transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously, however it is possible for multiple devices to function independently, either by responding only to a specific transmitted frequency, or through the use of a selective modulation technique such as pulse width modulation, or through encoding techniques such as time-division multiplexing.

A leadless pulse stimulator would be applied as follows. Utilizing current surgical techniques to access regions of the brain, a miniaturized receiver-stimulator device would be implanted into brain tissue or attached to the desired location in contact with brain tissue. Various techniques and tools for cranial access and probing of brain tissue have been described which would be adapted to facilitate delivery of the receiver-stimulator to these locations; the receiver-transmitter would incorporate means to provide permanent attachment to the implant site including possibly helical coils, barbs, tines, or the like. Functionally, the receiver-stimulator device comprises an ultrasound transducer to receive the acoustic energy and transform it into electrical energy, an electrical circuit to transform the alternating electrical energy into a direct current, and electrodes to transfer the electrical field energy between an electrode pair to the brain tissue and to the surrounding area.

Additionally, a controller-transmitter device is adapted for directional, vibrational energy transmission emitted by the device to intersect the implanted receiver-stimulator. In the implanted version, the controller-transmitter device containing the transmitting transducer is implanted typically just beneath the skin in a subcutaneous space. Alternatively, the controller-transmitter is adapted to be implanted as a structurally compliant device that retains the mechanical integrity of the skull and is implanted in the region of cranial access. Alternatively, the controller-transmitter is implanted beneath the skull but above the brain in the cranial space. If not implanted, the transducer portion of the transmitter would be placed over the skin directionally angled to the target region containing the receiver-stimulator with acoustic gel, or other means, used for coupling the acoustic energy to the skull.

In an alternative embodiment, the controller-transmitter device is incorporated into a device also providing conventional lead-based electrical stimulation, in a brain stimulation system, wherein a conventional lead/electrode system would provide stimulus to directly connected regions of the brain using leads and transmitting vibrational energy to provide stimulation to regions of the brain where receiver-stimulators are implanted.

The controller-transmitter device, would contain similar elements of most currently available stimulator systems including a power source, stimulation control and timing circuitry, physiologic sensing systems, a system to communicate with an outside console for data transmission, diagnostic, and programming functions typically through a radiofrequency (RF) link. Additionally, the controller-transmitter device would contain an ultrasound amplifier and an ultrasound transducer to generate acoustic energy, and transmit such energy in the general direction of the receiver-stimulator implanted in the brain. The duration, timing, and power of the acoustic energy transmission would be controlled as required, according to known electrophysiological parameters that are constructed for specific treatments for the brain.

A single receiver-stimulator device is implanted in the brain as described above for single-region stimulation; alternatively, it would be possible to implant a plurality of receiver-stimulator devices to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current implementations. Selecting multiple sites and regions for treatments would be greatly enhanced by eliminating the need to connect multiple electrode sites to the stimulation energy source by the use of multiple leads/wires connected to the electrodes.

These examples are representative but in no way limiting of the applications in which an electro-acoustic stimulator may be utilized in this invention to stimulate tissue in the brain to effect treatment of medical conditions.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

An example of such an electro-acoustic stimulation system as a brain stimulator is illustrated in FIGS. 1, 2, and 3.

In FIG. 1, a controller-transmitter device 1 containing circuitry to provide stimulation control and ultrasound transmission, plus means to communicate with an outside programmer 3 is implanted in the skull, either subcutaneously between the skull and the skin or as a replacement for skull bone removed during access of the cranial area. It is situated such that the directional angle of the transmitted ultrasound beam would intersect the receiver-stimulator 2. An ultrasound signal is transmitted by this device through intervening tissue to the receiver-stimulator device 2 containing means to receive this acoustic energy and convert it into an electrical waveform which may then be applied to the attached electrodes. In FIG. 1 this receiver-stimulator device 2 is shown embedded, in this one example, in a deep brain location near the thalamus. The receiver-stimulator device 2 is shown here as a small cylindrical or button-shaped device that would be affixed to the brain with an attaching coil or other method, similar to the means by which electrical lead wires are fixed to the brain in current stimulator systems. Optionally (not shown), the receiver-stimulator 2 could be deployed into the brain tissue. Also optionally (not shown), the receiver-stimulator device 2 could be incorporated into a expandable or self-expanding mechanical mesh that would stay located in the tissue by means of spring tension similar to a stent placement in a vascular application but rather held in place between tissue sections of the brain.

FIGS. 2a and 2b show more details of the system described above and shown in FIG. 1. In FIG. 2a the controller-transmitter device 1 comprises: a battery 10, one or more sensors 11, signal processing circuitry 12, a communications module 13, a control and timing module 14, an ultrasound amplifier 15, an ultrasound transducer 16. The battery 10 which provides power for the controller-transmitter may be of a type commonly used in implanted medical devices such as a lithium iodine cell or lithium silver vanadium oxide cell made by Greatbatch, Inc. or which is optionally a rechargeable battery. The one or more sensors 11 are used to detect physiological parameters. Sensors may be chosen to measure acute response or to measure chronic progression of response. Suitable sensors are known for the detection of electrical activity, impedance, temperature, motion, strain, pressure, and the like. These sensors being connected to signal processing circuitry 12 and used by the circuitry to adjust delivery of stimulation therapy or to communicate diagnostic information from the sensors. The communications module 13 provides a data path to allow the physician to set device parameters and to acquire diagnostic information about the patient and/or the device. The data path may be by an RF communication link, magnetic coupling, ultrasound pulses, or the like, and would communicate to and from an external unit 3. Device parameters would be used by the control and timing module 14. Device parameters would include adjustments to transmissions, such as power amplitude, pulse duration, duty cycle, and the like. The control and timing module 14 uses device parameters in conjunction with the acquired physiological data to generate the required control signals for the ultrasound amplifier 15 which in turn applies electrical energy to the ultrasound transducer 16 which in turn produces the desired acoustic beam. The controller-transmitter device 1 is encased in a hermetically sealed case 17 constructed of a biologically compatible material, typical of currently existing DBS devices.

Referring to FIG. 2b, the receiver-stimulator device 2, implanted in the path of the acoustic beam at the location where electrical stimulation is desired, contains an ultrasound transducer 20, an electrical circuit 21, and electrodes 22. Ultrasound transducer 20, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 21 which may be one of a type commonly known as an envelope detector, and which may have one of many known circuit configurations, for example a full-wave rectifier, a half-wave rectifier, a voltage doubler or the like. Electrical circuit 21 produces a voltage pulse with amplitude proportional to the amplitude of the transmitted ultrasound burst and with a pulse length generally equal to the length of the transmitted burst. The circuit 21 may also be of different configurations and function, and provide output signals having characteristics other than a pulse. This signal is applied then to electrodes 22 made typically of platinum, platinum-iridium, gold, or the like which may be incorporated onto the outer surface of the device, and thus in direct contact with the brain or within close proximity of brain which is to be treated by stimulation. Alternatively, the electrodes 22 are connected via wires to a main body that consists of the transducer 20 and electrical circuit 21 and the electrodes 22 are adapted to be shapeable, malleable configurations that conform to regions of the brain as flexible wraps or the like or that could be placed near the brain on the dura. Electrodes may be adapted that are round, long, segmented, etc. to increase surface area or to control current density at the electrode. Electrodes may be placed on opposing sides of the brain tissues or in linear alignment with the tissue or in any arrangement suitable for the size and location of the brain and the targeted brain stimulation site. The receiver-stimulator device 2 is also enclosed within a sealed case 23 of biologically compatible material Referring also to previously described FIGS. 2a and 2b, FIG. 3 provides detail representing example acoustic and electrical signals of the present system. FIG. 3 first depicts a train of electrical stimulation pulses 31 which have a desired width and are repeated at a desired interval. The controller-transmitter device 1 produces acoustic transmissions 32, for the desired stimulation pulse width and repeated at the desired stimulation pulse interval, which are emitted from the ultrasound transducer 16. Below the waveform 32 is shown an enlargement 33 of a single acoustic burst. This burst again has a desired width, a desired oscillation frequency F=1/t, and also a desired acoustic pressure indicated by the peak positive pressure P+ and peak negative pressure P−. The acoustic pressure wave, when striking the receiving transducer 20 of the receiver-stimulator device 2 generates an electrical signal 34 having frequency and burst length matching that of the transmitted waveform 33 and amplitude proportional to the transmitted acoustic pressure (~+/−P). This electrical waveform is then rectified and filtered by the circuit 21 producing the desired pulse 35 with length equal to the burst length of the transmitted waveform 33 and amplitude ($V_{PULSE}$) proportional to the amplitude of the electrical signal 34. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 21 could be configured to produce a direct current (DC) output or an alternating current (AC) output, or an output with any arbitrary waveform. Varying the use of signal information within the ultrasound transmission for pulse duration, pulse amplitude, and duty cycle would result in any type of burst sequencing or continuous delivery waveform effective for brain stimulation. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening tissue, with spatial location of the receiver-stimulator device with respect to the transmitted ultrasound beam as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to adjust automatically using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 4A:
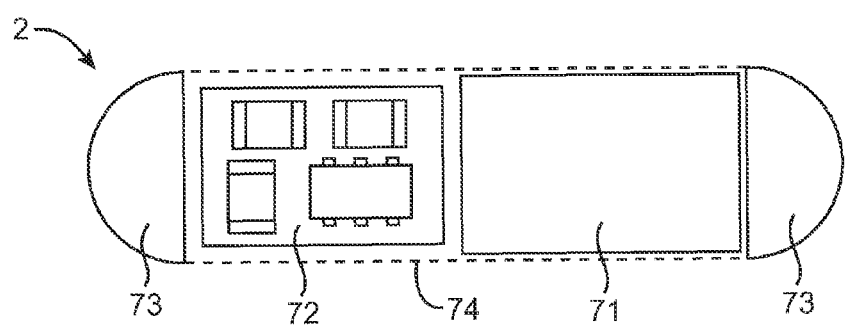
FIGS. 4a, 4b, and 4c are schematic illustrations showing components of the present invention.
Figure 4B:
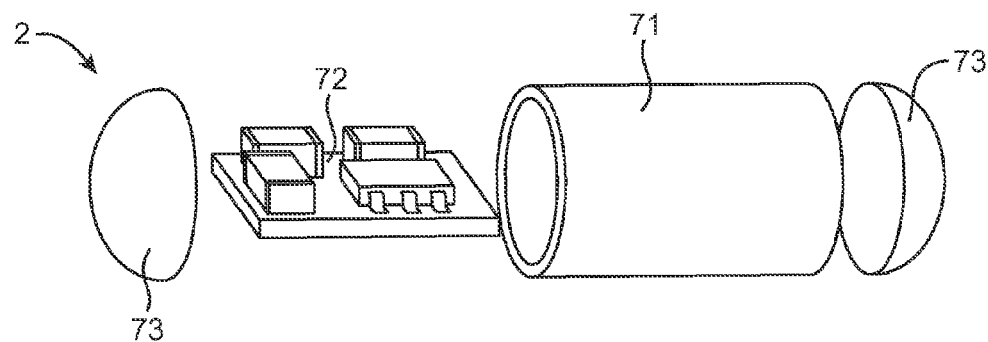
Figure 4C:
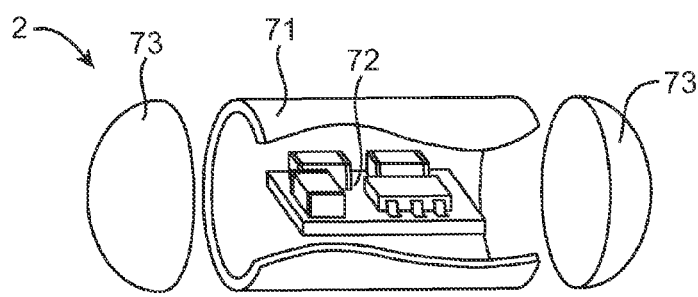

FIGS. 4a through 4c illustrate two embodiments of a small implantable receiver-stimulator of a cylindrical profile, suitable perhaps for placement by catheter, stylet, or by injection through a hypodermic needle. FIG. 4a shows in plan view and 4b in perspective view such a receiver-stimulator 2 having a hollow, cylindrical ultrasound transducer 71, a circuit assembly 72 comprising the detector, and two electrodes 73 at either end of the assembly. It can be appreciated that any number of electrodes may be adapted to this embodiment. The transducer 71 would be made of an appropriate piezoelectric ceramic material, having two electrical activity contacts deposited on the outer and inner surfaces of the cylinder, respectively. The transducer and circuit would be encapsulated in an electrically insulating but acoustically transparent medium 74. The transducer 71 would be of a rigid piezoelectric material, typically a piezo-ceramic with electrodes deposited on the outer and inner surfaces of the cylinder. The circuit assembly 72 may be fabricated using known surface-mount or hybrid assembly techniques, upon either a fiberglass or ceramic substrate. Stimulation electrodes 73 would be fabricated of material commonly used in implanted electrodes, such as platinum, platinum-iridium, or the like. Necessary electrical wiring between the transducer, circuit board, and electrodes is not shown in these drawings. Typical dimensions of such a device would be 1.5 cm in length and 1.5 mm in diameter, and preferably smaller. Multiple electrodes could be adapted as appendages to the embodiment (not shown) or incorporated into fixation elements such as helical screws or barbs (not shown).

As shown in FIG. 4c, by using hybrid circuit techniques it may be possible to further miniaturize the circuit assembly 72 such that it would fit inside the hollow interior of the transducer 71. This would have the benefit of substantially reducing the length of the finished device.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A system for stimulating brain tissue comprising:
an implantable acoustic controller-transmitter configured to be implanted in a body of a patient and generate acoustic energy, wherein the controller-transmitter comprises acoustic transducers disposed in a housing and one or more physiological sensors disposed on an external surface of the housing, and wherein the one or more physiological sensors are configured to detect one or more physiological parameters directly from the body;
an implantable acoustic receiver-stimulator comprising a stimulation electrode assembly adapted to be in direct contact with brain tissue, wherein the receiver-stimulator is configured to receive and convert the acoustic energy into an electrical stimulation output delivered to the brain tissue by the stimulation electrode assembly, wherein the electrical stimulation output has at least one of pulse amplitude, pulse duration, duty cycle, and timing, wherein the controller-transmitter is configured to periodically sense the electrical stimulation output of the receiver-stimulator and adjust acoustic energy transmission accordingly in order to compensate for changes in the electrical stimulation output of the receiver-stimulator; and
an external programmer configured to program one or more settings of the controller-transmitter.

2. A system as in claim 1, wherein the receiver-stimulator comprises an acoustic receiver which receives acoustic energy and generates alternating current, means for converting the alternating current to a pre-determined waveform, and electrodes adapted to deliver the pre-determined waveform to stimulate brain tissue.

3. A system as in claim 2 wherein the implantable receiver-stimulator is adapted to be located at one of the following locations: under the skull, within the brain, on the brain, on the dura, or in the cranial space in close proximity to the brain.

4. A system as in claim 2 wherein the implantable receiver-stimulator is adapted to be located at a predetermined brain stimulation site, said predetermined brain stimulation site being selected from the group consisting of the pallido-thalamic axons (AL), the lenticulo-thalamic fiber pathway (LT), substantia nigra pars reticulata (SNr), external segment of globus pallidus (GPe), subthalamic to pallidal fiber tracts, putamen, putamen to GPe fibers, the ventrobasal (VB) area of the thalamus, the ventral posteromedial (VPM) nucleus, the ventral posterolateral nucleus (VPL), the ventrolateral nucleus (VL), the posterior complex of the thalamus (PO), the motor cortex, the sensory cortex, the cingulate gyrus, the medial lemniscus, the internal capsule, the periventricular grey (PVG) matter, the periaqueductal grey (PAG) matter, the nucleus of tractus solitarius (NTS), the sub thalamic nucleus, the hippocampus, the medial thalamus, the temporal lobe, and any ischemic area of the brain tissue.

5. A system as in claim 4 wherein the implantable receiver-stimulator is adapted to be placed and secured to stimulate brain sites effective in altering brain activity as a therapeutic treatment.

6. A system as in claim 1, wherein the controller-transmitter comprises a power source, control and timing circuitry to provide a stimulation signal, means for converting the stimulation signal to an acoustic energy signal, and means for transmitting the acoustic energy signal to the receiver-stimulator.

7. A system as in claim 6 wherein control circuitry includes the one or more-physiological sensors in order to adjust timing of stimulation.

8. A system as in claim 7 wherein the control circuitry is configured to detect electrical brain activity and time the stimulation signal to synchronize or desynchronize the brain activity.

9. A system of claim 8 wherein the control circuitry is configured to process an electrogram signal of brain activity from electrodes in contact with tissue located on the exterior surface of the controller-transmitter.

10. A system of any one of claims 3 to 9, further comprising at least one additional receiver-stimulator device.

11. A system of claim 10, wherein the system is programmed to activate the receiver-stimulator devices sequentially.

12. A system as in claim 10, wherein the system is programmed to activate the receiver-stimulator devices simultaneously.

13. A system for stimulating brain tissue as in claim 1, adapted to transmit and receive acoustic energy wherein the frequency of the acoustic energy is between 20 kHz and 10 MHz, the burst length is between 3 cycles and a continuous burst, the duty cycle is between 0.01% and 100.00%, and the mechanical index is less than 1.9.

14. A method as in claim 1, wherein the housing is a hermetically sealed housing.

15. A system as in claim 14, wherein the sensors have a portion within the housing and a portion external to the housing.

16. A system as in claim 15, wherein the sensors are directly connected to the signal processing circuitry of the controller-transmitter.

17. A system as in claim 1, wherein the external programmer transmits a radiofrequency signal and the controller-transmitter comprises circuitry for receiving the radiofrequency signal.

18. A system as in claim 1, wherein the receiver-stimulator consists essentially of an ultrasound transducer which generates a stimulation signal in response to the acoustic energy transmitted by the receiver-stimulator, circuitry which rectifies the stimulation signal, and at least one electrode which delivers the rectified signal as the electrical stimulation output to brain tissue.

* * * * *